(12) United States Patent
Dexter et al.

(10) Patent No.: US 8,383,548 B2
(45) Date of Patent: Feb. 26, 2013

(54) STABLE MIXTURES OF MICROENCAPSULATED AND NON-ENCAPSULATED PESTICIDES

(75) Inventors: Robin W. Dexter, Yardley, PA (US); Hong Liu, Pennington, NJ (US)

(73) Assignee: FMC Corporation, Philadelphia, PA (US)

( * ) Notice: Subject to any disclaimer, the term of this patent is extended or adjusted under 35 U.S.C. 154(b) by 937 days.

(21) Appl. No.: 12/279,607

(22) PCT Filed: Feb. 21, 2007

(86) PCT No.: PCT/US2007/062456
§ 371 (c)(1), (2), (4) Date: Aug. 15, 2008

(87) PCT Pub. No.: WO2007/101019
PCT Pub. Date: Sep. 7, 2007

(65) Prior Publication Data
US 2010/0234225 A1     Sep. 16, 2010

Related U.S. Application Data

(60) Provisional application No. 60/776,126, filed on Feb. 23, 2006.

(51) Int. Cl.
| | | |
|---|---|---|
| *A01N 43/64* | (2006.01) | |
| *A01N 37/36* | (2006.01) | |
| *A01N 43/40* | (2006.01) | |
| *A01N 43/76* | (2006.01) | |
| *A01N 59/26* | (2006.01) | |
| *A01N 47/36* | (2006.01) | |
| *A01N 25/34* | (2006.01) | |
| *A01N 57/00* | (2006.01) | |
| *A61K 9/16* | (2006.01) | |
| *A61K 9/50* | (2006.01) | |
| *A61K 9/52* | (2006.01) | |

(52) U.S. Cl. ........ 504/134; 504/116; 504/118; 504/127; 504/128; 504/175; 504/211; 504/234; 504/244; 504/254; 504/262; 504/270; 504/271; 504/307; 504/319; 504/323; 504/330; 504/342; 504/355; 424/402; 424/406; 424/408; 424/457; 424/497

(58) Field of Classification Search .................. 504/134, 504/116, 118, 127, 128, 175, 211, 234, 244, 504/254, 262, 270, 271, 307, 319, 323, 330, 504/342, 355; 424/402, 406, 408, 457, 497
See application file for complete search history.

(56) References Cited

U.S. PATENT DOCUMENTS

| | | | |
|---|---|---|---|
| 4,956,129 A | 9/1990 | Scher et al. | |
| 5,229,122 A | 7/1993 | Chadwick et al. | |
| 5,583,089 A | 12/1996 | Winston | |
| 5,583,090 A | 12/1996 | Stern et al. | |
| 5,665,678 A | 9/1997 | Essinger, Jr. | |
| 5,783,520 A | 7/1998 | Anderson et al. | |
| 6,218,339 B1 * | 4/2001 | Becker et al. | 504/140 |
| 6,440,902 B1 * | 8/2002 | Szamosi | 504/138 |
| 6,583,087 B2 | 6/2003 | Ueda | |

FOREIGN PATENT DOCUMENTS

EP    0792100 B1    11/1995

OTHER PUBLICATIONS

Dargar, Ratna V., "Clomazone Measurement by Enzyme-Linked Immunosorbent Assay" Journal of Agricultural and Food Chemistry (1991), 39, pp. 813-819.

* cited by examiner

*Primary Examiner* — Richard Schnizer
(74) *Attorney, Agent, or Firm* — FMC Corporation

(57) ABSTRACT

The present invention is directed to a composition comprising i) a microencapsulated pesticide, ii) a dispersant selected from the group consisting of a lignin, b) a lignosulfonate salt and c) a lignosulfonate salt combined with the sodium salt of substituted naphthalene sulfonate formaldehyde polymer, iii) a salt selected from the group consisting of magnesium sulfate, sodium chloride, sodium nitrate and calcium chloride, and iv) a non-encapsulated pesticide. The present invention is also directed to methods of making and using the compositions of the present invention.

17 Claims, No Drawings

STABLE MIXTURES OF MICROENCAPSULATED AND NON-ENCAPSULATED PESTICIDES

This application claims the benefit of U.S. Provisional Application No. 60/776,126, filed Feb. 23, 2006.

FIELD OF THE INVENTION

The present invention relates to the field of agrochemical compositions and formulations.

BACKGROUND OF THE INVENTION

To enable the efficient elimination or controlling of unwanted pests and plants, it is desirable to use effective chemical formulations of pesticides. Compositions containing multiple pesticides are desirable in agricultural, specialty and related endeavors due to broadening the spectrum or range of unwanted pest and plant species killed or controlled.

Due to the desirability of having a composition with the above mentioned properties, it is useful to use combinations of pesticides or combinations of a herbicide with another herbicide, insecticide, fungicide etc., to obtain enhanced control of the numerous weeds and pests with a single application. Combinations of pesticides, formulation methods and commercial products of certain combinations of herbicides are known and available. Such combinations are known and available as mixed solutions of the active ingredients in emulsifiable concentrate (EC) formulations, but frequently more complex formulations are required to combine active ingredients with widely different physical properties in order to avoid chemical and physical stability problems.

Clomazone, the common name for 2-[(2-chlorophenyl) methyl]-4,4-dimethyl-3-isoxazolidinone, a highly effective herbicide, is also highly volatile. Clomazone applied to the soil in a target area may move to adjacent areas causing whitening or bleaching of plants near treated fields. Microencapsulated clomazone is used in order to reduce volatility by 50% or less, thereby reducing off-site plant injury, while maintaining a satisfactory level of herbicidal activity in the target area. Although microencapsulated formulations of water-insoluble pesticides control the volatility of pesticides, for example Command 3ME, which is the commercially available microencapsulated formulation of clomazone (FMC Corporation), it has been found that when admixed with a second active substance, external to the microcapsules, the mixture is not stable. It can be shown that if the external substance is oleophilic, attracting water-insoluble substances, then the contents of the microcapsule may be rapidly extracted from the capsules and into the oily disperse phase. Attempts to prepare stable liquid combinations of water-insoluble pesticide microcapsules, such as clomazone, with other active ingredients in the same package have been unsuccessful, either because the volatility of the pesticide is affected by the movement from inside the microcapsule to the oily disperse phase or the composition is not stable.

SUMMARY OF THE INVENTION

The present invention provides new pesticide compositions that have retained volatility control and broad spectrum effects.

Specifically, the present invention is directed to a composition comprising i) a microencapsulated pesticide, ii) a dispersant selected from the group consisting of a) a lignin, b) a lignosulfonate salt and c) a lignosulfonate salt combined with the sodium salt of a substituted naphthalene sulfonate formaldehyde polymer, iii) a salt selected from the group consisting of magnesium sulfate, sodium chloride, sodium nitrate and calcium chloride, and iv) a non-encapsulated pesticide. The present invention is also directed to methods of making and using the compositions of the present invention.

DETAILED DESCRIPTION OF THE INVENTION

The present invention relates to a composition comprising i) a microencapsulated pesticide, ii) a dispersant selected from the group consisting of a) a lignin, b) a lignosulfonate salt and c) a lignosulfonate salt combined with the sodium salt of substituted naphthalene sulfonate formaldehyde polymer, iii) a salt selected from the group consisting of magnesium sulfate, sodium chloride, sodium nitrate and calcium chloride, and iv) a non-encapsulated pesticide.

The microencapsulated pesticide is preferably a water-insoluble pesticide. Micro encapsulation is a process in which the herbicidal compound may be encapsulated in a shell of polyurea, polyamide or amide-urea copolymer as disclosed in EP 0792100 B1 and U.S. Pat. No. 5,583,090, the disclosures of which are incorporated herein by reference. Preferably, the microencapsulated pesticide is selected from the group consisting of bifenthrin, cypermethaln, permethrin, zeta-cypermethrin, clomazone, cadusafos, carbosulfan, pendimethalin and dimethenamid. Even more preferably, the microencapsulated pesticide is clomazone. The microencapsulated pesticide can be present in an amount of from 1% by weight to 10% by weight of all components in the total composition, preferably an amount of from 1% by weight to 6% by weight of all components in the total composition.

The non-encapsulated pesticide is preferably selected from the group consisting of napropamide, linuron and metribuzin. More preferably, the non-encapsulated pesticide is linuron or metribuzin. The non-encapsulated pesticide can be present in an amount of from 20% by weight to 35% by weight of all components in the total composition.

The dispersant can be present in an amount of from 0.5% by weight to 10% by weight of all components in the total composition, preferably in an amount of from 1% by weight to 4% by weight of all components in the total composition. A lignin is a complex natural polymer found in wood. Modified lignins are obtained by treatment with alkali or by sulfonation. Such modified lignins are obtained as by-products derived from the wood pulping process. Preferably, the dispersant is a lignosulfonate salt, for example, sodium lignosulfonate salts such as Reax 88, Reax100M, Polyfon H, Polyfon O, polyfon T, Polyfon F, available from MeadWestvaco Corporation and Ufoxane 3A, available from LignoTech USA, Inc. or a calcium lignosulfonate salt, for example, Norlig BD available from LignoTech USA, Inc. The lignosulfonate salt can be used in combination with the sodium salt of a substituted naphthalene sulfonate formaldehyde polymer. An example of a suitable sodium salt of a substituted naphthalene sulfonate formaldehyde polymer is Morwet D-425 powder, available from Akzo Nobel.

The salt can be present in an amount of from 4% by weight to 20% by weight of all components in the total composition, preferably in an amount of from 7% by weight to 15% by weight of all components in the total composition. The salt can be present as a single salt or a mixture of salts, for example, sodium chloride in an amount of from 4% to 20%, sodium nitrate in an amount of from 4% to 20%, or sodium nitrate and calcium chloride in a combined amount of from 4% to 20%.

The composition can further comprise an anti-foam agent; a pH balancing agent; a thickening agent and an anti-microbial agent. Preferably, the anti-foam agent is a silicone emulsion, for example, Dow Corning AF Emulsion available from Dow Corning Corporation, present in an amount of from 0.001% by weight to 0.5% by weight of all components in the total composition. Preferably, the pH balancing agent is acetic acid present in an amount of from 0.001% by weight to 0.5% by weight of all components in the total composition. Preferably, the thickening agent is xanthan gum, for example, Kelzan S available from CP Kelco, present in an amount of from 0.02% by weight to 0.25% by weight of all components in the total composition. Preferably the antimicrobial agent is Proxel GXL available from Avecia or Legend MK available from Rohm and Haas Corporation, and is present in an amount of from 0.001% by weight to 0.5% by weight of all components in the total composition, A preferred embodiment of the present invention is i) a composition comprising microencapsulated clomazone, ii) a dispersant selected from the group consisting of a) a lignin, b) a lignosulfonate salt and c) a lignosulfonate salt combined with the sodium salt of substituted naphthalene sulfonate formaldehyde polymer, iii) a salt selected from the group consisting of magnesium sulfate, sodium chloride, sodium nitrate and calcium chloride, and iv) a non-encapsulated pesticide selected from the group consisting of linuron and metribuzin.

Another embodiment of the present invention is a composition suitable for use in preparing a mixture of a microencapsulated pesticide and a non-encapsulated pesticide comprising i) a microencapsulated pesticide, ii) a dispersant selected from the group consisting of a) a lignin, b) a lignosulfonate salt and c) a lignosulfonate salt combined with the sodium salt of substituted naphthalene sulfonate formaldehyde polymer, and iii) a salt selected from the group consisting of magnesium sulfate, sodium chloride, sodium nitrate and calcium chloride.

Another embodiment of the present invention is a method for the control of unwanted pests or plants comprising applying a pesticidally effective amount of the composition of the present invention to an area where such control is desired.

Yet another embodiment of the present invention is a process for preparing the composition comprising combining the non-encapsulated pesticide with a dispersant and water, milling the resultant mixture, and combining the milled mixture with the encapsulated pesticide and a salt.

As used in this specification and unless otherwise indicated the term "pesticide" refers to a molecule or combination of molecules that repels, inhibits or kills insects and/or unwanted plants, and can be used for crop protection, edifice protection, turf protection or protection of a person. The term "insecticide" refers to a molecule or combination of molecules that repels, inhibits or kills insects, and can be used for crop protection, edifice protection, turf protection or protection of a person. The term "herbicide" refers to a molecule or combination of molecules that inhibits or otherwise kills unwanted plants, such as, but not limited to, deleterious or annoying weeds, broadleaf plants, grasses, sedges, and can be used for crop protection, edifice protection or turf protection. The term "pesticidally effective amount" means an amount necessary to produce an observable pesticidal effect on unwanted pests and/or plant growth, including the effects of necrosis, death, growth inhibition, reproduction inhibition, inhibition of proliferation, and removal, destruction, or otherwise diminishing the occurrence and activity of unwanted pests and/or plants.

The term "ambient temperature" as utilized herein shall generally mean any suitable temperature found in a laboratory or other working quarter, and is generally not below about 15° C. nor above about 30° C. The term "linuron" means N'-(3,4-dichlorophenyl)-N-methoxy-N-methylurea. The term "metribuzin" means 4-amino-6-(1,1-dimethylethyl)-3-(methylthio)-1,2,4-triazin-5(4H)-one. The term "napropamide" means N,N-diethyl-2-(1-naphthalenyloxy) propanamide. The term "clomazone" means 2-[(2-chlorophenyl)methyl]-4,4-dimethyl-3-isoxazolidinone. The term "Command 3ME" means a commercial microencapsulated formulation of clomazone available from FMC Corporation.

As used herein, "% by weights of components in the total composition" includes the wt % of all liquid and solid components in the composition.

The compositions of the present invention are further illustrated by the examples below. Unless otherwise specified in the examples, the linuron used in the examples below contained 97% active ingredient, the metribuzin used contained 90% active ingredient, the Command 3ME used contained 31.4% active ingredient and the napropamide used contained 94.2% active ingredient. The examples serve only to illustrate the invention and should not be interpreted as limiting since further modifications of the disclosed invention will be apparent to those skilled in the art. All such modifications are deemed to be within the scope of the invention as defined in the claims.

Example 1

Composition of Linuron and Command 3ME with Sodium Nitrate and Calcium Chloride

A mixture of 30.92 parts of linuron, 2.3 parts of lignosulfonate sodium salt (Reax 88B available from MeadWestvaco in Charleston, S.C.) and 0.035 parts of Dow antifoam AF in 36.49 parts of water was milled to the a particle size distribution where 90% of the particles were less than about 6 microns.

To 69.745 parts of this milled base were added, while stirring, 11.5 parts of sodium nitrate, 10.5 parts of calcium chloride, 0.02 parts of a preservative (Proxel GXL available from Avecia, Inc. in Wilmington Del.), 0.2 parts of acetic acid, 0.035 parts of Dow antifoam and 8.0 parts of a 1% aqueous solution of xantham gum (Kelzan S available from CP Kelco in Wilmington Del.).

Finally, to 68.3 parts of the mixture prepared above were added, while stirring, 11.75 parts of Command 3ME, 9.54 parts of a 1% aqueous solution of xantham gum (Kelzan S available from CP Kelco in Wilmington Del.) and 10.41 parts of a solution containing 70% water, 15% calcium chloride and 15% sodium nitrate.

The resultant density of the final mixture was about 1.21 grams per milliliter. The clomazone to linuron ratio was about 45 g/l:248 g/l.

Example 2

Composition of Metribuzin and Command 3ME with Sodium Chloride

A mixture of 38.9 parts of metribuzin, 2.7 parts of lignosulfonate sodium salt (Reax 88B available from Westvaco in Charleston, S.C.), 0.4 parts of acetic acid and 0.2 parts of Dow antifoam AF in 57.8 parts of water was milled to the a particle size distribution where 90% of the particles were less than about 6 microns.

To 70.0 parts of this milled base were added, while stirring, 15.0 parts of sodium chloride, 0.02 parts of a preservative (Proxel GXL available from Avecia, Inc. in Wilmington Del.), 6.98 parts of water and 8.0 parts of a 1% aqueous solution of xantham gum (Kelzan S available from CP Kelco in Wilmington Del.).

Finally, to 83.0 parts of the mixture prepared above were added, while stirring, 17.0 parts of Command 3ME. The resultant density of the final mixture was about 1.17 grams per milliliter. The clomazone to metribuzin ratio was about 62 g/l:238 g/l.

Example 3

Composition of Linuron and Command 3ME with Sodium Nitrate and Calcium Chloride

A mixture of 30.92 parts of linuron, 2.3 parts of lignosulfonate sodium salt (Reax 88B available from Westvaco in Charleston, S.C.) and 0.035 parts of Dow antifoam AF in 36.49 parts of water was milled to the a particle size distribution where 90% of the particles were less than about 6 microns.

To 69.745 parts of this milled base were added, while stirring, 11.5 parts of sodium nitrate, 10.5 parts of calcium chloride, 0.02 parts of a preservative (Proxel GXL available from Avecia, Inc. in Wilmington Del.), 0.2 parts of acetic acid, 0.035 parts of Dow antifoam and 8.0 parts of a 1% aqueous solution of xantham gum (Kelzan S available from CP Kelco in Wilmington Del.).

Finally, to 83.0 parts of the mixture prepared above were added, while stirring, 7.9 parts of Command 3ME and 9.1 parts of a 1% aqueous solution of xantham gum (Kelzan S available from CP Kelco in Wilmington Del.).

The resultant density of the final mixture was about 1.22 grams per milliliter. The clomazone to linuron ratio was about 30.2 g/l:303 g/l.

Example 4

Composition of Napropamide and Command 3ME with Sodium Nitrate and Calcium Chloride A mixture of 28.93 parts of napropamide, 2.0 parts of lignosulfonate sodium salt (Reax 88B available from Westvaco in Charleston, S.C.), 0.15 parts of acetic acid and 0.125 parts of Dow antifoam AF in 68.80 parts of water was milled to the a particle size distribution where 90% of the particles were less than about 6 microns.

To 77.56 parts of this milled base were added, while stirring, 4.43 parts of sodium nitrate, 4.43 parts of calcium chloride, 5.82 parts of Command 3ME, 3.88 parts of water and 3.88 parts of a 1% aqueous solution of xantham gum (Kelzan S available from CP Kelco in Wilmington Del.).

The resultant density of the final mixture was about 1.10 grams per milliliter. The clomazone to napropamide ratio was about 1.98 g/l:230.6 g/l.

Example 5

Composition of Linuron and Command 3ME with Sodium Nitrate and Calcium Chloride

A mixture of 30.92 parts of linuron, 2.3 parts of lignosulfonate sodium salt (Reax 88B available from Westvaco in Charleston, S.C.) and 0.035 parts of Dow antifoam AF in 36.49 parts of water was milled to the a particle size distribution where 90% of the particles were less than about 6 microns.

To 69.745 parts of this milled base were added, while stirring, 11.5 parts of sodium nitrate, 10.5 parts of calcium chloride, 0.02 parts of a preservative (Proxel GXL available from Avecia, Inc. in Wilmington Del.), 0.2 parts of acetic acid, 0.035 parts of Dow antifoam and 8.0 parts of a 1% aqueous solution of xantham gum (Kelzan S available from CP Kelco in Wilmington Del.).

Finally, to 68.28 parts of the mixture prepared above were added, while stirring, 11.75 parts of Command 3ME, 8.0 parts of a 1% aqueous solution of xantham gum (Kelzan S available from CP Kelco in Wilmington Del.) and 11.98 parts of water.

The clomazone to linuron ratio was about 45 g/l:250 g/l.

Example 6

Composition of Napropamide and Command 3ME with Sodium Nitrate

A mixture of 23.36 parts of napropamide, 1.55 parts of lignosulfonate sodium salt (Reax 88B available from Westvaco in Charleston, S.C.), 0.19 parts of acetic acid, 0.04 parts antimicrobial agent (legend MK) and 0.10 parts of Dow antifoam PL97-1517 in 44.00 parts of water was milled to the a particle size distribution where 90% of the particles were less than about 6 microns.

To 71.88 parts of this milled base were added, while stirring, 8.80 parts of sodium nitrate, 6.25 parts of Command 3ME, 1.31 parts of water and 14.00 parts of a 1% aqueous solution of xantham gum (Kelzan S available from CP Kelco in Wilmington Del.).

The resultant density of the final mixture was about 1.13 grams per milliliter. The clomazone to napropamide ratio was about 23 g/l:250 g/l.

Example 7

Composition of Metribuzin and Command 3ME with Calcium Chloride and Sodium Nitrate A mixture of 40.00 parts of metribuzin, 2.7 parts of lignosulfonate sodium salt (Reax 88B available from Westvaco in Charleston, S.C.), 0.86 parts of acetic acid and 0.6 parts of Dow antifoam AF in 55.85 parts of water was milled to the a particle size distribution where 90% of the particles were less than about 6 microns.

To 78.0 parts of this milled base were added, while stirring, 10.0 parts of sodium nitrate, 10.0 parts calcium chloride and 2.0 parts of a 1% aqueous solution of xantham gum (Kelzan S available from CP Kelco in Wilmington Del.).

Finally, to 77.6 parts of the mixture prepared above were added, while stirring, 20.0 part of Command 3ME. The resultant density of the final mixture was about 1.07 grams per milliliter. The clomazone to metribuzin ratio was about 60 g/l:233 g/l.

Example 8

Composition of Metribuzin and Command 3ME with Magnesium Sulfate

A mixture of 40.00 parts of metribuzin, 2.7 parts of lignosulfonate sodium salt (Reax 88B available from Westvaco in Charleston, S.C.), 0.86 parts of acetic acid and 0.6 parts of Dow antifoam AF in 55.85 parts of water was milled to the a particle size distribution where 90% of the particles were less than about 6 microns.

To 84.0 parts of this milled base were added, while stirring, 15.0 parts of magnesium sulfate and 1.0 part of a 1% aqueous solution of xantham gum (Kelzan S available from CP Kelco in Wilmington Del.).

Finally, to 72.0 parts of the mixture prepared above were added, while stirring, 20.0 parts of Command 3ME. The resultant density of the final mixture was about 1.13 grams per milliliter. The clomazone to metribuzin ratio was about 60 g/l:233 g/l.

Comparative Example 9

Composition of Metribuzin and Command 3ME

A mixture of 254.0 grams of commercially available metribuzin (Sencor 4 flowable herbicide available from Bayer Crop Science) was added to 100.0 grams of Command 3ME was stirred for 30 minutes. The resulting formulation was stored at 50° C. for one week and then examined. The formulation had gelled and was determined to be unusable.

Example 10

Volatility Testing

Laboratory tests for the volatility of clomazone from the test compositions were carried out in the following manner. Sufficient unsterilized topsoil to conduct the test was passed twice through a 14-mesh sieve to remove large particles and debris. The fine particles were then removed through a 30-mesh sieve, leaving behind topsoil of intermediate-sized particles. This intermediate-sized topsoil, 240 grams, was spread uniformly to a thickness of about one to two millimeters over an area of about 27.9 cm. by 41.3 cm in a tray measuring 32.4 cm. by 45.7 by 1.9 cm. The topsoil was then sprayed from an overhead track sprayer calibrated to deliver 20 gallons of water per acre. The spray mix consisted of sufficient test composition to provide 0.0712 gram of clomazone active ingredient in 20 mL of water. In this manner the test composition was applied to the soil at a rate of 1.0 kg a.i. (clomazone active ingredient)/ha. Immediately after treatment, the soil was enclosed in a glass jar, where it remained briefly until used.

For each test composition, four 22 mm by 300 mm glass chromatography columns, each containing a coarse sintered glass barrier at the bottom, were connected through their bottom ends to a multi-port air manifold, which delivered equal air pressure simultaneously to a number of columns. In each of the four columns was placed 59 grams of the treated topsoil, which filled about 200 mm of the column length. In the top of each column was then placed a polyurethane foam plug designed to fit inside a 21 to 26 mm diameter tube. As soon after the soil treatment as the columns could be set up, a slow stream of air (0.75 to 1.00 liter per minute per column) from the multi-port air manifold was passed through the soil in each column, causing the volatilized clomazone to collect on the polyurethane foam plug. The time between the soil treatment and the start of the air flow was about one hour. The air flow was continued for about 18 hours.

Following the 18 hour collection period, the polyurethane foam plug from each column was placed in a 20 mL plastic syringe. The polyurethane foam plug was thoroughly extracted by drawing 15 mL of methanol into the syringe and through the plug, forcing the methanol extract into a beaker, and repeating the process several times. A 0.04 mL aliquot of the 15 mL sample was diluted with 0.96 mL of methanol and 1.0 mL of water. A 0.1 mL aliquot of this solution was analyzed for clomazone content using an enzyme-linked immunosorbent assay (ELISA), a method reported by R. V. Darger et al. (J. Agr. and Food Chem., 1991, 39, 813-819). The total clomazone content of the foam plug, expressed in micrograms (mg), of each sample was recorded and compared to the clomazone content of the sample from the standard, Command 4 EC Herbicide (FMC Corporation). The percent volatility was calculated by the following formula and is summarized in the table below:

% Volatility=(mg clomazone in test composition extract÷mg clomazone in standard extract)×100.

A % volatility value of less than 50% at ambient temperature is preferred. More preferred are compositions having a % volatility of less than 50% after storage at greater temperatures.

| Composition of Example Number | Composition storage time and temperature | % Volatility as compared to standard |
|---|---|---|
| | % Volatility of Clomazone | |
| 2 | 1 month at ambient temperature | 23% |
| 3 | 1 month at ambient temperature | 16% |
| 5 | 1 month at ambient temperature | 18% |
| 6 | 1 month at 40° C. | 26% |
| 7 | 1 month at ambient temperature | 14% |
| 8 | 1 month at ambient temperature | 18% |
| 8 | 1 month at 40° C. | 52% |
| Control* | 1 month at 40° C. | 20% |
| Gamit Top/Command Top** | 1 month at ambient temperature | >57% |

*Control = Command 3ME commercial formulation available from FMC Corporation.
**A mixture of technical napropamide, milled with surfactants and water, combined with Command 3ME (Trade names Gamit Top/Command Top) acquired from United Phosphorus Limited.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A composition comprising:
   i) microencapsulated clomazone,
   ii) a dispersant selected from the group consisting of a) a lignin, b) a lignosulfonate salt and c) a lignosulfonate salt combined with a sodium salt of substituted naphthalene sulfonate formaldehyde polymer; and
   iii) magnesium sulfate; and
   iv) a non-encapsulated pesticide selected from the group consisting of napropamide, linuron and metribuzin.

2. The composition of claim 1, wherein the non-encapsulated pesticide is linuron or metribuzin.

3. The composition of claim 1, wherein the dispersant is present in an amount of from 0.5% by weight to 10% by weight of all components in the total composition.

4. The composition of claim 3, wherein the dispersant is present in an amount of from 1% by weight to 4% by weight of all components in the total composition.

5. The composition of claim 1, wherein the magnesium sulfate is present in an amount of from 4% by weight to 20% by weight of all components in the total composition.

6. The composition of claim 5, wherein the magnesium sulfate is present in an amount of from 7% by weight to 15% by weight of all components in the total composition.

7. The composition of claim 1, wherein the microencapsulated pesticide is present in an amount of from 1% by weight to 10% by weight of all components in the total composition.

8. The composition of claim 7, wherein the microencapsulated clomazone is present in an amount of from 1% by weight to 6% by weight of all components in the total composition.

9. The composition of claim 1, wherein the non-encapsulated pesticide is present in an amount of from 20% by weight to 35% by weight of all components in the total composition.

10. The composition of claim 1, further comprising an anti-foam agent.

11. The composition of claim 1, further comprising a pH balancing agent.

12. The composition of claim 11, wherein the pH balancing agent is acetic acid present in an amount of from 0.001% by weight to 0.5% by weight of all components in the total composition.

13. The composition of claim 1, further comprising a thickening agent.

14. The composition of claim 13, wherein the thickening agent is xanthan gum present in an amount of from 0.02% by weight to 0.25% by weight of all components in the total composition.

15. A composition suitable for combination with a non-encapsulated pesticide comprising:
   i) microencapsulated clomazone,
   ii) a dispersant selected from the group consisting of a) a lignin, b) a lignosulfonate salt and a lignosulfonate salt combined with the sodium salt of substituted naphthalene sulfonate formaldehyde polymer; and
   iii) magnesium sulfate.

16. A method for the control of unwanted plants comprising applying a pesticidally effective amount of the composition of claim 1 to an area where such control is desired.

17. A process for preparing a composition of claim 1 comprising:
   a) combining the non-encapsulated pesticide with a dispersant and water;
   b) milling the mixture of step a); and
   c) combining the milled mixture of step b) with the encapsulated clomazone and magnesium sulfate.

* * * * *